US00PP31863P2

(12) United States Plant Patent
NeSmith

(10) Patent No.: US PP31,863 P2
(45) Date of Patent: Jun. 16, 2020

(54) SOUTHERN HIGHBUSH BLUEBERRY PLANT NAMED 'TH-1125'

(50) Latin Name: *Vaccinium corymbosum*
Varietal Denomination: TH-1125

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,818

(22) Filed: Jan. 16, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Klarquist Sparkman, LLP

(57) ABSTRACT

The new variety 'TH-1125' ripens around early May in south Georgia. The fruit of the new variety 'TH-1125' are large, firm and have good flavor. The new variety 'TH-1125' is vigorous with an estimated chilling requirement of about 250 to 300 hours at or below approximately 7° C. The asexually reproduced variety is reliably propagated vegetatively.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-1125' is a southern highbush blueberry plant that is a *Vaccinium corymbosum.*

Variety denomination: The new southern highbush blueberry plant claimed is of the variety denominated 'TH-1125'.

BACKGROUND OF THE INVENTION

The present invention relates to the discovery of a new and distinct cultivar of southern highbush blueberry plant botanically known as a *Vaccinium corymbosum* and herein referred to as 'TH-1125', as herein described and illustrated.

The new blueberry plant variety 'TH-1125' was selected in Griffin, Ga. in 2007. The new variety 'TH-1125' ripens around late April in southern Georgia. The fruit of the new variety 'TH-1125' are large with favorable firmness and good flavor. The new variety 'TH-1125' has acceptable yield and is vigorous with an estimated chilling requirement of about 250-300 hours at or below 7° C.

Pedigree and history: 'TH-1125' was selected in 2007 at Griffin, Ga., originating from a cross of 'Camellia' (female parent, U.S. Plant Pat. No. 18,151) X 'Palmetto' (male parent, U.S. Plant Pat. No. 16,756) made in 2004 by D. Scott NeSmith. The 'TH-1125' was first asexually propagated at Griffin, Ga. in 2007 by vegetative stem cuttings. The selection has been tested in plantings at research farms at Alapaha, Ga. and Griffin, Ga. since 2009, and, in trial plantings in Peru beginning in 2013.

Observations have shown that the unique features of this new *Vaccinium corymbosum* 'TH-1125' are stable and have reproduced true to type in successive generations.

SUMMARY OF THE INVENTION

The new blueberry plant variety 'TH-1125' has not been observed under all possible environmental conditions. The phenotype may vary somewhat with variations in environment and cultural practices, such as temperature and light intensity, without, however, any variance in genotype.

The following traits have been repeatedly observed in Alapaha and Griffin, Ga., and are determined to be the unique characteristics of the new blueberry plant variety 'TH-1125':

1. Large berry size;
2. Early ripening;
3. Good berry flavor;
4. Favorable berry firmness; and
5. Remarkable plant vigor.

The new variety 'TH-1125' can be compared to the early ripening southern highbush blueberry varieties 'TH-819' (U.S. Plant Pat. No. 24,696), 'Rebel' (U.S. Plant Pat. No. 18,138), 'Suziblue' (U.S. Plant Pat. No. 21,167), and 'Camellia' (U.S. Plant Pat. No. 18,151).

Comparison: 'TH-1125' is early season and begins ripening after the early variety 'TH-819' in south Georgia, but before 'Rebel'. 'TH-1125' has large, very firm berries with good flavor as compared to 'TH-819', 'Rebel', and 'Camellia' at Alapaha, Ga. (Table 1) and as compared to 'Camellia', 'Rebel', and 'Suziblue' in Griffin, Ga. (Table 2). Table 3 describes berry weight, firmness, and Brix for 'TH-1125' as compared to the 'Rebel', 'Suziblue', and 'Camellia' southern highbush blueberry cultivars for the years 2011 and 2013. 'TH-1125' had a larger berry weight than the 'Camellia'. 'TH-1125' has a two-year average Brix comparable to 'Camellia' and higher than 'Rebel' and 'Suziblue' cultivars. 'TH-1125' also has a lower chill requirement than 'Palmetto' and 'Camellia'.

While a major attraction of 'TH-1125' is fruit quality, the variety does have an additional favorable attribute. Preliminary trials in regions of low latitude (Peru) have indicated that 'TH-1125' may perform well as an evergreen or ever bearing variety. These regions receive atypical (if any) "chill hours"; and finding varieties that produce well in such regions is a challenge. Observations have revealed that 'TH-1125' appears to have the potential to adapt to such conditions.

TABLE 1

Table 1 sets forth three-year average ratings of fruit and plant characteristics of 'TH-1125' and standard cultivars 'Camellia', 'TH-819', and 'Rebel' from 2011, 2012, and 2016, growing in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2009.

| Berry and | Alapaha location | | | |
|---|---|---|---|---|
| plant attributes | 'TH-1125' | 'Camellia' | 'Rebel' | 'TH-819' |
| Berry size | 8.8 | 8.8 | 7.8 | 7.2 |
| Berry scar | 7.3 | 7.0 | 7.5 | 7.5 |
| Berry color | 7.5 | 8.5 | 7.5 | 7.5 |
| Berry firmness | 9.0 | 7.5 | 7.8 | 7.2 |
| Berry flavor | 7.5 | 7.8 | 6.8 | 7.5 |
| Cropping | 4.5 | 5.8 | 6.0 | 4.0 |
| Plant vigor | 9.5 | 9.5 | 8.0 | 8.5 |
| Date of 50% flowering | Feb. 26 | Mar. 5 | Feb. 25 | Feb. 20 |
| Date of 50% ripening | April 23 | May 4 | April 26 | April 18 |
| Fruit development period (days) | 59 | 61 | 60 | 57 |

TABLE 2

Table 2 sets forth two-year average ratings of fruit and plant characteristics of 'TH-1125' and standard cultivars 'Camellia', 'Suziblue', and 'Rebel' from 2011-2012, growing in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2009.

| Berry and | Griffin location | | | |
|---|---|---|---|---|
| plant attributes | 'TH-1125' | 'Camellia' | 'Rebel' | 'Suziblue' |
| Berry size | 8.2 | 8.2 | 7.3 | 8.2 |
| Berry scar | 7.8 | 7.0 | 7.3 | 7.5 |
| Berry color | 7.8 | 8.0 | 7.0 | 7.0 |
| Berry firmness | 8.8 | 7.5 | 7.3 | 8.2 |
| Berry flavor | 7.8 | 7.3 | 6.5 | 7.0 |
| Cropping | 6.5 | 8.0 | 5.5 | 7.2 |
| Plant vigor | 9.5 | 9.5 | 5.8 | 7.5 |
| Date of 50% flowering | Mar. 1 | Mar. 6 | Mar. 1 | Mar. 2 |
| Date of 50% ripening | May 2 | May 16 | May 3 | May 5 |
| Fruit development period (days) | 61 | 70 | 62 | 63 |

TABLE 3

Table 3 sets forth two-year average berry weight, firmness, and Brix for 'Camellia', 'Suziblue', and 'Rebel' cultivars and 'TH-1125' grown in Griffin, GA during 2011 and 2013.

| | 'TH-1125' | 'Camellia' | 'Suziblue' | 'Rebel' |
|---|---|---|---|---|
| Berry wt (g/berry) | 2.15 | 2.08 | 2.62 | 1.65 |
| Brix (%) | 13.6 | 13.7 | 13.2 | 11.5 |
| Firmness (g/mm) | 186 | 156 | 188 | 170 |

BRIEF DESCRIPTION OF THE FIGURES

The accompanying photographic illustrations show typical specimens in full color of the foliage, flowering, and fruit of the new variety 'TH-1125'. The colors are as nearly true as is reasonably possible in a color representation of this type.

BOTANICAL DESCRIPTION

Figure 1A:
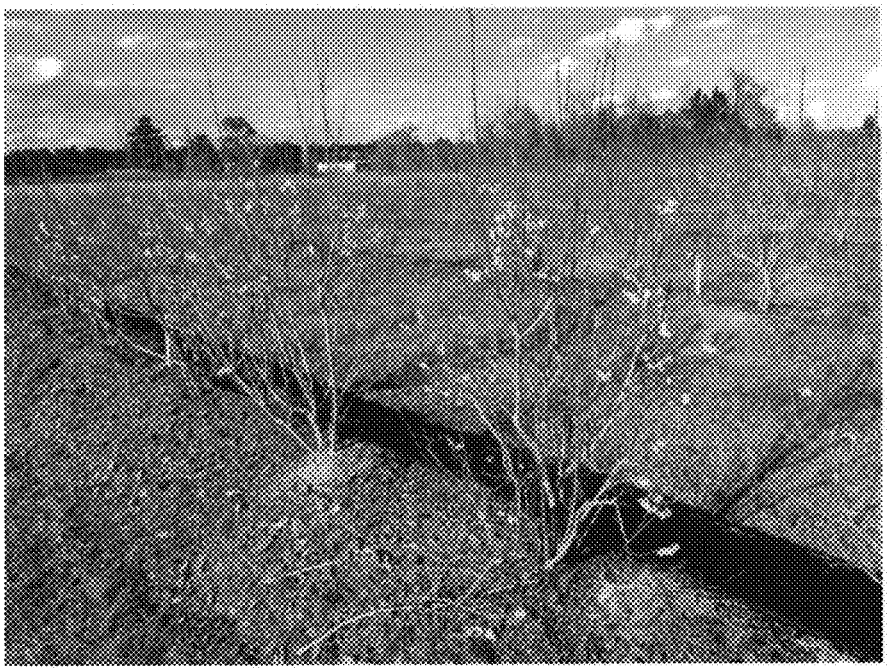
FIGS. 1A and 1B show photographs of six year old plants of the new variety 'TH-1125' during flowering at Alapaha, Ga.
Figure 1B:
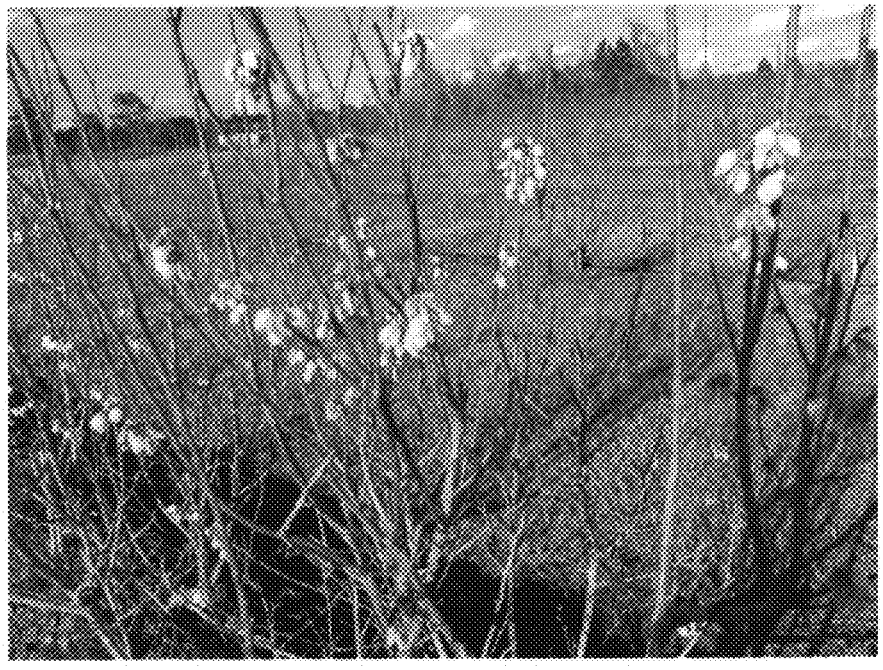
Figure 2:
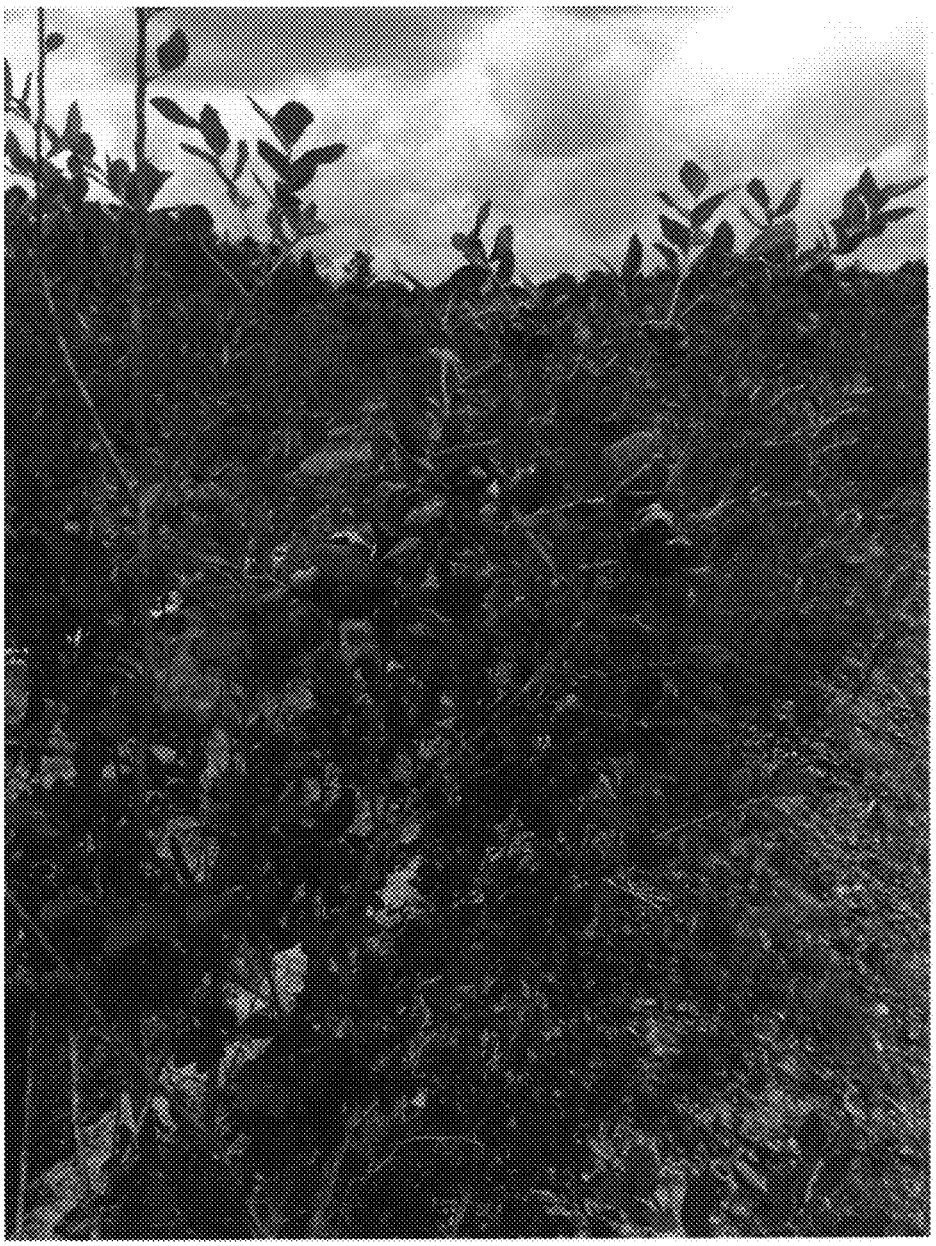
FIG. 2 is a photograph of six year old plants of the new variety 'TH-1125' during fruit ripening at Alapaha, Ga.
Figure 3:
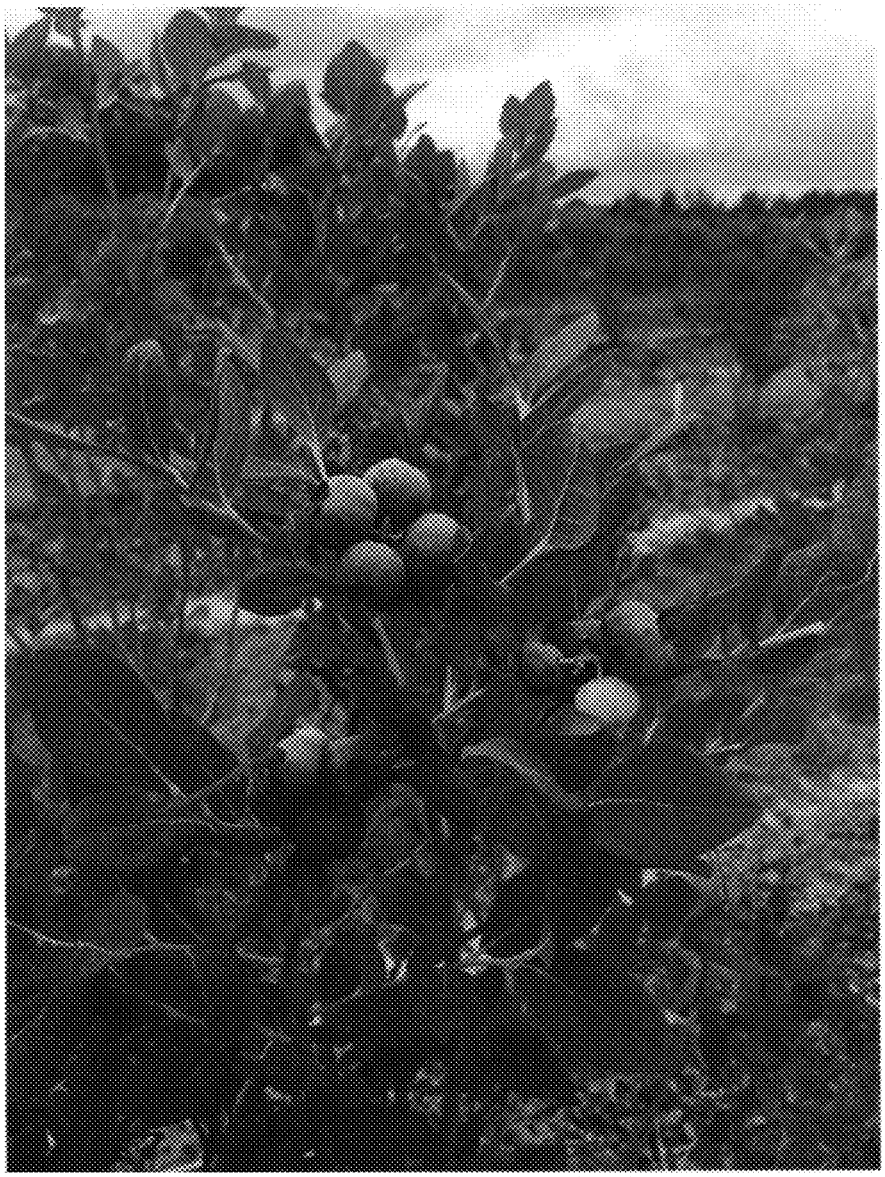
FIG. 3 is a close up photograph of fruit clusters of the new variety 'TH-1125'.
Figure 4A:
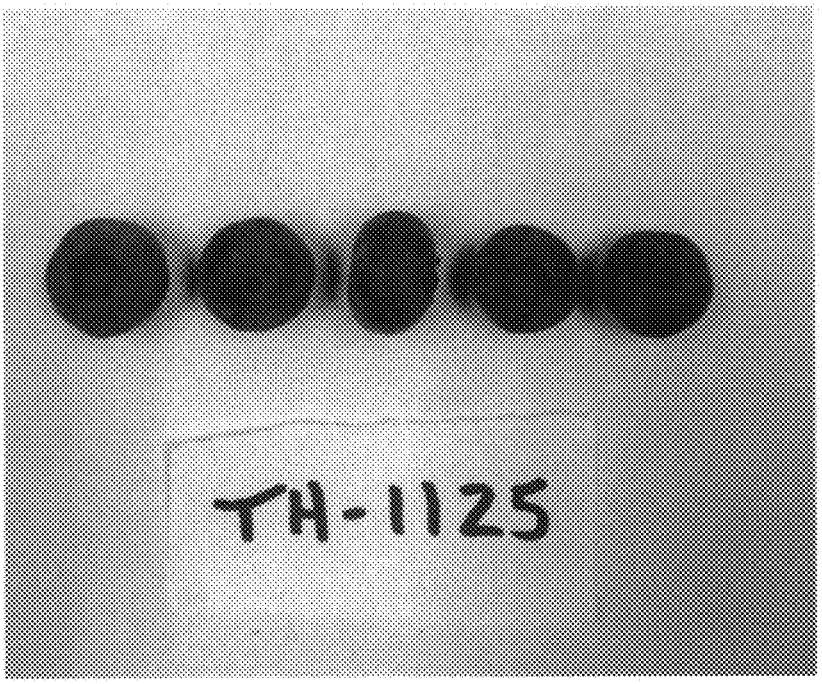
FIGS. 4A and 4B are photographs of harvested berries of the new variety 'TH-1125'; with photograph 4B showing a bisected berry.
Figure 4B:
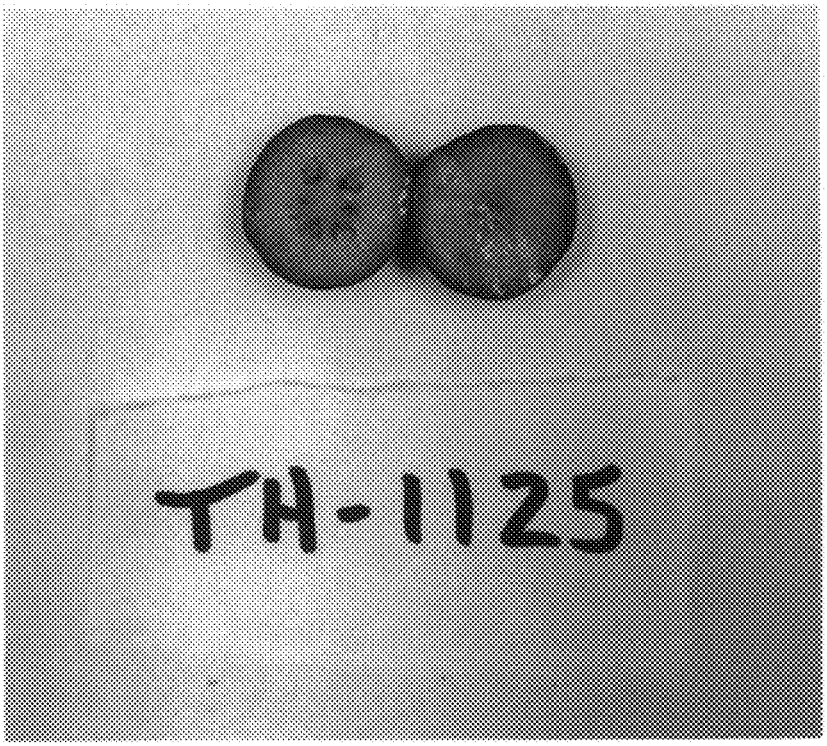

Throughout this specification, color names beginning with a small letter signify that the name of that color, as used in common speech, is aptly descriptive. Color names beginning with a capital letter designate values based upon The R.H.S. Colour Chart, $5^{th}$ edition published in 2007 by The Royal Horticultural Society, London, England.

The following is a detailed description of the botanical and pomological characteristics of the new variety 'TH-1125'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 3 to about 6 years old.

Plant:

*Size.*—1.2 to 1.6 m tall by 3 years. Plants grown under highly productive soil and fertility conditions have exceeded 2.0 m tall in 4 years. The plant crown, or base, is very narrow, typically 15 to 25 cm in diameter. The upper portion of the plant canopy exceeds 1.0 m in diameter by 3 to 4 years.

*Growth habit.*—Strongly upright, vertical growth, with 2 to 4 main canes arising from the crown, and multiple branching of shoots from those canes above ground.

*Growth.*—Moderately vigorous.

*Productivity.*—Medium crop and yield, averaging 5 to 7 lbs of fruit per plant each year for plants 3 years and older grown under well-fertilized and irrigated field conditions.

*Hardiness.*—Not fully determined. Has been grown at locations in GA, having USDA hardiness zones 8a and 8b and in an area in Peru that does not experience freezing temperatures.

*Chilling requirement.*—250 to 300 hours, more or less, of temperatures at or below 7° C. to induce normal leafing and flowering during the spring under conventional dormant production systems. The chill requirement is less than the male parent, 'Palmetto' (U.S. Plant Pat. No. 16,756; 400 to 450 hours of chilling required), and the female parent, 'Camellia' (U.S. Plant Pat. No. 18,151; 500 to 550 hours of chilling required). 'TH-1125' has shown a propensity for evergreen production with little or no chilling when grown under lower latitude locations.

*Leafing.*—Plants tend to break sufficient leaf buds simultaneously with or shortly after anthesis.

*Fruiting wood.*—Twigs 10 to 15 cm in length with internode lengths of 15 to 25 mm common.

*Canes.*—Diameter: Main cane base diameter 20 to 30 mm, two-year-old cane diameter 10 to 15 mm, current season wood diameter 4 to 8 mm. Color: Main cane color most near Brown RHS N200C to Grey RHS 201C for base of canes, two-year-old cane transitions from Yellow Green RHS 145A to Greyed Orange RHS 177B. Yellow Green RHS 145A in current season wood.

*Disease and pest resistance.*—None observed.

Foliage:

*Leaf color.*—Healthy mature leaves. Top side: Green RHS 137C to RHS 138A. Under side: Yellow Green RHS 147C.

*Leaf arrangement.*—Alternate, simple.

*Leaf shape.*—Elliptic.

*Leaf surface.*—Glaucous, both upper and lower surfaces.

*Leaf margins.*—Nearly smooth.

*Leaf venation.*—Reticulate.

*Leaf apices.*—Broadly acute.

*Leaf bases.*—Acute.

*Leaf dimensions.*—Length: 60.0 to 70.0 mm. Width: 30.0 to 35.0 mm.

*Petioles.*—Small. Length: 3.0 to 5.0 mm. Width: 1.5 to 2.0 mm. Color: Yellow Green RHS 145B. Vegetative buds: Typically begin to burst in mid to late February in Southeast GA.

Flowers:

*Date of* 50% *anthesis.*—February 22 to February 28 in southeast Georgia (5 year average). Flowers begin to open in early to mid-February in Southeast GA.

*Flower shape.*—Urceolate.

*Flower bud number.*—Medium, averaging 3 to 5 buds per fruiting shoot.

*Flowers per cluster.*—4 to 7 common.

*Flower fragrance.*—None.

*Corolla tube.*—Color: White RHS NN155C (open flower). Length: 9.5 to 11.5 mm. Width: 7.0 to 7.5 mm. Aperture width: 3.0 to 4.0 mm. Anthocyanin: Medium prior to flower opening (RHS 63C to 62B), but generally absent when corollas are fully expanded.

*Flower peduncle.*—Length: 8.5 to 12.0 mm. Color: Yellow Green RHS 145C.

*Flower pedicle.*—Length: 3.0 to 4.5 mm. Color: Green RHS 138C.

*Calyx* (*with sepals*).—Diameter: 6.5 to 7.5 mm. Color: Green RHS 137C.

*Stamen.*—Length: 7.0 to 7.5 mm. Number per flower: 10. Filament color: Yellow Green RHS 145D.

*Style.*—Length: 8.5 to 9.5 mm. Color: Yellow Green RHS 145B.

*Pistil.*—Length: 10.5 to 12.0 mm. Ovary color (exterior): Green RHS 138B.

*Anther.*—Length: 4.0 to 4.8 mm. Number: 10. Color: Greyed Orange RHS 165B.

*Pollen.*—Abundance: Medium to high. Color: Yellow White RHS 158A.

*Self-compatibility.*—The cultivar has a moderate degree of self-compatibility.

Fruit:

*Date of* 50% *maturity.*—April 22 to 28 in southeast Georgia (5 year average).

*Fruit development period.*—57 to 62 days.

*Fruit bloom intensity.*—Medium to strong.

*Fruiting.*—One year old shoots and current shoots depending upon climate where plant is grown.

*Berry color.*—With wax: Violet Blue RHS 97B to RHS 98D. With wax removed: Black RHS 203C.

*Berry surface wax abundance.*—Medium to high.

*Berry flesh color.*—Yellow Green RHS 145D.

*Berry weight.*—First harvest: 2.8 to 3.5 g. Second harvest: 1.8 to 2.2 g.

*Berry size.*—Height from calyx to scar: 12.0 to 14.0 mm. Diameter: 17.0 to 21.0 mm.

*Berry shape.*—Semi-disk shape.

*Fruit stem scar.*—Small to medium, dry, with little or no tearing upon harvest, scar size typically ranges from 0.8 mm to 1.2 mm.

*Calyx.*—Depth shallow, 1.0 to 2.0 mm; width 6.0 to 9.0 mm; sepals typically not highly visible, slightly turned outward and flat to semi-erect when present, <1 mm.

*Berry firmness.*—Very firm.

*Berry flavor and texture.*—Flavor moderately acidic flavor, semi-sweet; crisp texture.

*Berry acidity.*—Fruit acidity is medium to high.

*Storage quality.*—Very good. Berries remain firm and retain good quality for about 20 to 28 days in proper storage.

*Suitability for mechanical harvesting.*—Unknown.

*Uses.*—Primarily to be used as fresh fruit for shipping and processing markets.

Seed:

*Seed abundance in fruit.*—Medium with 10 to 20 fully developed seeds per berry.

*Seed color.*—Greyed Orange RHS 165B.

*Seed dry weight.*—44.1 mg per 100 seed.

*Seed size.*—1.8 to 2.1 mm long.

What is claimed is:

1. A new and distinct variety of southern highbush blueberry plant named 'TH-1125', as illustrated and described herein.

* * * * *